United States Patent
Biedermann et al.

(10) Patent No.: US 9,962,193 B2
(45) Date of Patent: May 8, 2018

(54) BONE ANCHORING DEVICE, TOOL AND METHOD FOR ASSEMBLING THE SAME AND TOOL FOR USE WITH THE SAME

(71) Applicant: Biedermann Technologies GmbH & Co. KG, Donaueschingen (DE)

(72) Inventors: Lutz Biedermann, VS-Villingen (DE); Martin Meer, Vöhringen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 0 days. days.

(21) Appl. No.: 15/405,071

(22) Filed: Jan. 12, 2017

(65) Prior Publication Data

US 2017/0189074 A1    Jul. 6, 2017

Related U.S. Application Data

(63) Continuation of application No. 15/018,826, filed on Feb. 8, 2016, now Pat. No. 9,572,600, which is a (Continued)

(30) Foreign Application Priority Data

Aug. 20, 2009  (EP) .................................... 09168328

(51) Int. Cl.
*A61B 17/70* (2006.01)
*A61B 17/00* (2006.01)

(52) U.S. Cl.
CPC ...... *A61B 17/7037* (2013.01); *A61B 17/7032* (2013.01); *A61B 17/7082* (2013.01);
(Continued)

(58) Field of Classification Search
CPC ........................ A61B 17/7037; A61B 17/7032
See application file for complete search history.

(56) References Cited

U.S. PATENT DOCUMENTS 5,672,176 A * 9/1997 Biedermann ...... A61B 17/7032
606/271
5,716,356 A * 2/1998 Biedermann ...... A61B 17/7002
606/271

(Continued)

FOREIGN PATENT DOCUMENTS

CN          101264030 A      9/2008
DE    10 2005 021 879 A1    11/2006

(Continued)

OTHER PUBLICATIONS

European Search Report for Application No. EP 09 16 8328, dated Jun. 24, 2010, 13 pages.

(Continued)

*Primary Examiner* — Ellen C Hammond
*Assistant Examiner* — Stuart S Bray
(74) *Attorney, Agent, or Firm* — Lewis Roca Rothgerber Christie LLP

(57) ABSTRACT

A bone anchoring device includes an anchoring element having a shaft for anchoring in the bone and a head, a receiving part formed in one piece, and a pressure element formed in one piece. The receiving part has a seat for receiving the head and an outer channel for receiving a rod to be connected to the anchoring element, which is pivotable with respect to the receiving part and can be fixed at an angle by exerting pressure via the pressure element onto the head. The pressure element is movable in the receiving part and includes an inner channel for receiving the rod and a spring element that engages a portion of the receiving part via a detent connection so that the pressure element can be held in a position that allows pivoting of the anchoring element. The spring element is formed by at least a first portion of one of two side walls forming the inner channel, the first portion being spaced apart from a second portion of the one side (Continued)

wall by a slot. At least a portion of the detent connection is located on the one side wall.

9 Claims, 5 Drawing Sheets

Related U.S. Application Data continuation of application No. 12/856,251, filed on Aug. 13, 2010, now Pat. No. 9,254,150.

(60) Provisional application No. 61/235,493, filed on Aug. 20, 2009.

(52) U.S. Cl.
CPC ............ *A61B 2017/00526* (2013.01); *A61B 2017/00716* (2013.01)

(56) References Cited

U.S. PATENT DOCUMENTS

| | | | | |
|---|---|---|---|---|
| 5,728,098 | A * | 3/1998 | Sherman | A61B 17/7032 606/269 |
| 5,954,725 | A | 9/1999 | Sherman et al. | |
| 6,010,503 | A * | 1/2000 | Richelsoph | A61B 17/7032 606/278 |
| 6,132,434 | A | 10/2000 | Sherman et al. | |
| 6,254,602 | B1 * | 7/2001 | Justis | A61B 17/7032 606/272 |
| 6,355,040 | B1 | 3/2002 | Richelsoph et al. | |
| 6,454,773 | B1 | 9/2002 | Sherman et al. | |
| 6,471,705 | B1 * | 10/2002 | Biedermann | A61B 17/7032 606/271 |
| 6,554,834 | B1 * | 4/2003 | Crozet | A61B 17/7037 606/272 |
| 7,211,086 | B2 | 5/2007 | Biedermann et al. | |
| 7,291,151 | B2 * | 11/2007 | Alvarez | A61B 17/7037 606/305 |
| 7,322,981 | B2 * | 1/2008 | Jackson | A61B 17/7037 606/266 |
| 7,604,655 | B2 * | 10/2009 | Warnick | A61B 17/7035 606/265 |
| 7,682,377 | B2 * | 3/2010 | Konieczynski | A61B 17/7032 606/266 |
| 7,699,876 | B2 * | 4/2010 | Barry | A61B 17/7037 606/266 |
| 7,828,829 | B2 * | 11/2010 | Ensign | A61B 17/7037 606/287 |
| 7,875,065 | B2 * | 1/2011 | Jackson | A61B 17/7035 606/266 |
| 8,062,340 | B2 * | 11/2011 | Berrevoets | A61B 17/7032 606/270 |
| 8,123,785 | B2 * | 2/2012 | Weaver | A61B 17/025 606/272 |
| 8,257,396 | B2 * | 9/2012 | Jackson | A61B 17/7037 606/246 |
| 8,409,255 | B2 * | 4/2013 | Richelsoph | A61B 17/7037 606/264 |
| 8,435,266 | B2 * | 5/2013 | Richelsoph | A61B 17/7014 606/257 |
| 8,518,082 | B2 * | 8/2013 | Sicvol | A61B 17/7032 606/246 |
| 8,926,671 | B2 * | 1/2015 | Biedermann | A61B 17/7032 606/268 |
| 2003/0100904 | A1 * | 5/2003 | Biedermann | A61B 17/7032 606/272 |
| 2003/0125741 | A1 * | 7/2003 | Biedermann | A61B 17/7032 606/278 |
| 2003/0167058 | A1 * | 9/2003 | Shluzas | A61B 17/7032 606/270 |
| 2004/0097933 | A1 * | 5/2004 | Lourdel | A61B 17/7032 606/266 |
| 2004/0236330 | A1 * | 11/2004 | Purcell | A61B 17/7037 606/266 |
| 2005/0080420 | A1 * | 4/2005 | Farris | A61B 17/7037 606/261 |
| 2006/0089644 | A1 * | 4/2006 | Felix | A61B 17/7037 606/250 |
| 2006/0293664 | A1 * | 12/2006 | Schumacher | A61B 17/7037 606/254 |
| 2007/0043378 | A1 * | 2/2007 | Kumar | A61B 17/7082 606/104 |
| 2007/0118123 | A1 * | 5/2007 | Strausbaugh | A61B 17/7032 606/272 |
| 2007/0270842 | A1 * | 11/2007 | Bankoski | A61B 17/00234 606/86 A |
| 2007/0288004 | A1 * | 12/2007 | Alvarez | A61B 17/7032 606/86 A |
| 2008/0045970 | A1 * | 2/2008 | Saidha | A61B 17/8615 606/104 |
| 2008/0200918 | A1 * | 8/2008 | Spitler | A61B 17/7082 606/104 |
| 2008/0215100 | A1 * | 9/2008 | Matthis | A61B 17/7032 606/309 |
| 2008/0243185 | A1 * | 10/2008 | Felix | A61B 17/7032 606/246 |
| 2009/0069853 | A1 * | 3/2009 | Schumacher | A61B 17/7032 606/301 |
| 2009/0163962 | A1 * | 6/2009 | Dauster | A61B 17/7032 606/305 |
| 2010/0145394 | A1 * | 6/2010 | Harvey | A61B 17/7032 606/302 |
| 2010/0198272 | A1 * | 8/2010 | Keyer | A61B 17/7037 606/302 |
| 2011/0046683 | A1 * | 2/2011 | Biedermann | A61B 17/7035 606/305 |
| 2011/0053114 | A1 * | 3/2011 | Shimoda | A61C 7/36 433/173 |
| 2012/0029569 | A1 * | 2/2012 | Iott | A61B 17/7032 606/264 |
| 2012/0221057 | A1 * | 8/2012 | Zhang | A61B 17/7023 606/264 |
| 2012/0277799 | A1 * | 11/2012 | Winslow | A61B 17/7005 606/264 |
| 2012/0277800 | A1 * | 11/2012 | Jackson | A61B 17/7037 606/265 |
| 2012/0303064 | A1 * | 11/2012 | Walker | A61B 17/7037 606/270 |
| 2015/0282842 | A1 * | 10/2015 | Beyar | A61L 27/446 606/273 |
| 2017/0189074 | A1 * | 7/2017 | Biedermann | A61B 17/7037 |

FOREIGN PATENT DOCUMENTS

| | | |
|---|---|---|
| EP | 0947174 A2 | 10/1999 |
| EP | 1 570 794 A1 | 9/2005 |
| EP | 1 743 584 A1 | 1/2007 |
| EP | 2 111 811 A1 | 10/2009 |
| WO | WO 2006/116437 A2 | 11/2006 |
| WO | WO 2006/130179 A2 | 12/2006 |
| WO | WO 2007/025132 A2 | 3/2007 |
| WO | WO 2008/008511 A2 | 1/2008 |
| WO | WO 2009/015100 A2 | 1/2009 |

OTHER PUBLICATIONS

Extended European Search Report for Application No. EP 13 19 9788, dated Jul. 1, 2014, 12 sheets.
Partial European Search Report for Application No. EP09168328, dated Jan. 25, 2010.
Office action issued by the USPTO dated Dec. 5, 2011 for U.S. Appl. No. 12/709,375, 7 pages.
Office action issued by the USPTO dated Jul. 10, 2012 for U.S. Appl. No. 12/709,375, 6 pages.
Office action issued by the USPTO dated Sep. 13, 2013 for U.S. Appl. No. 12/709,375, 6 pages.
Office action issued by the USPTO dated Jun. 4, 2014 for U.S. Appl. No. 12/709,375, 5 pages.

(56) References Cited

OTHER PUBLICATIONS

Office action issued by the USPTO dated Jul. 29, 2014 for U.S. Appl. No. 12/855,395, 8 pages.
Office action issued by the USPTO dated Oct. 18, 2013 for U.S. Appl. No. 12/855,395, 10 pages.
Office action issued by the USPTO dated Jan. 15, 2013 for U.S. Appl. No. 12/855,395, 10 pages.

* cited by examiner

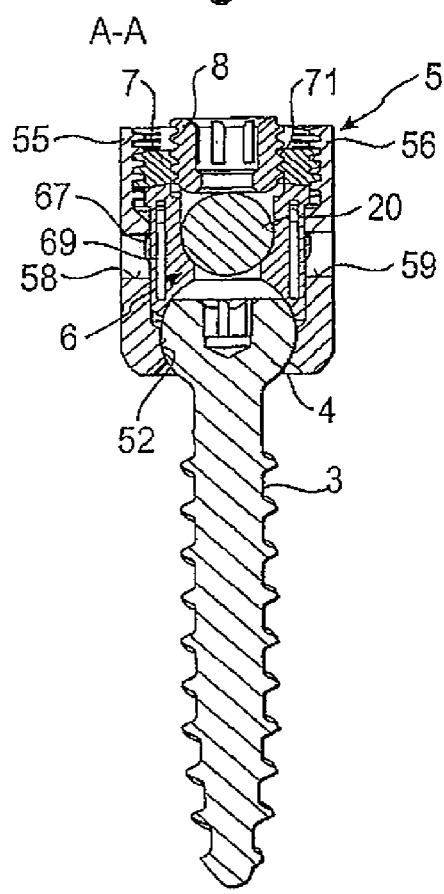
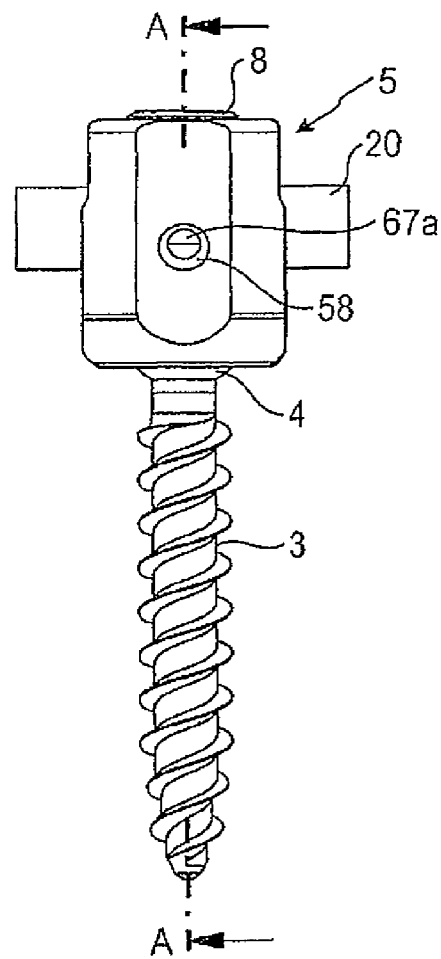
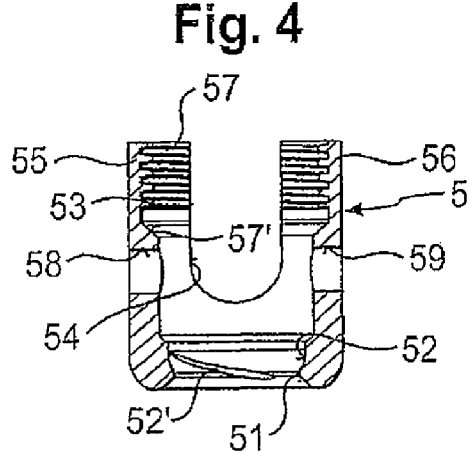

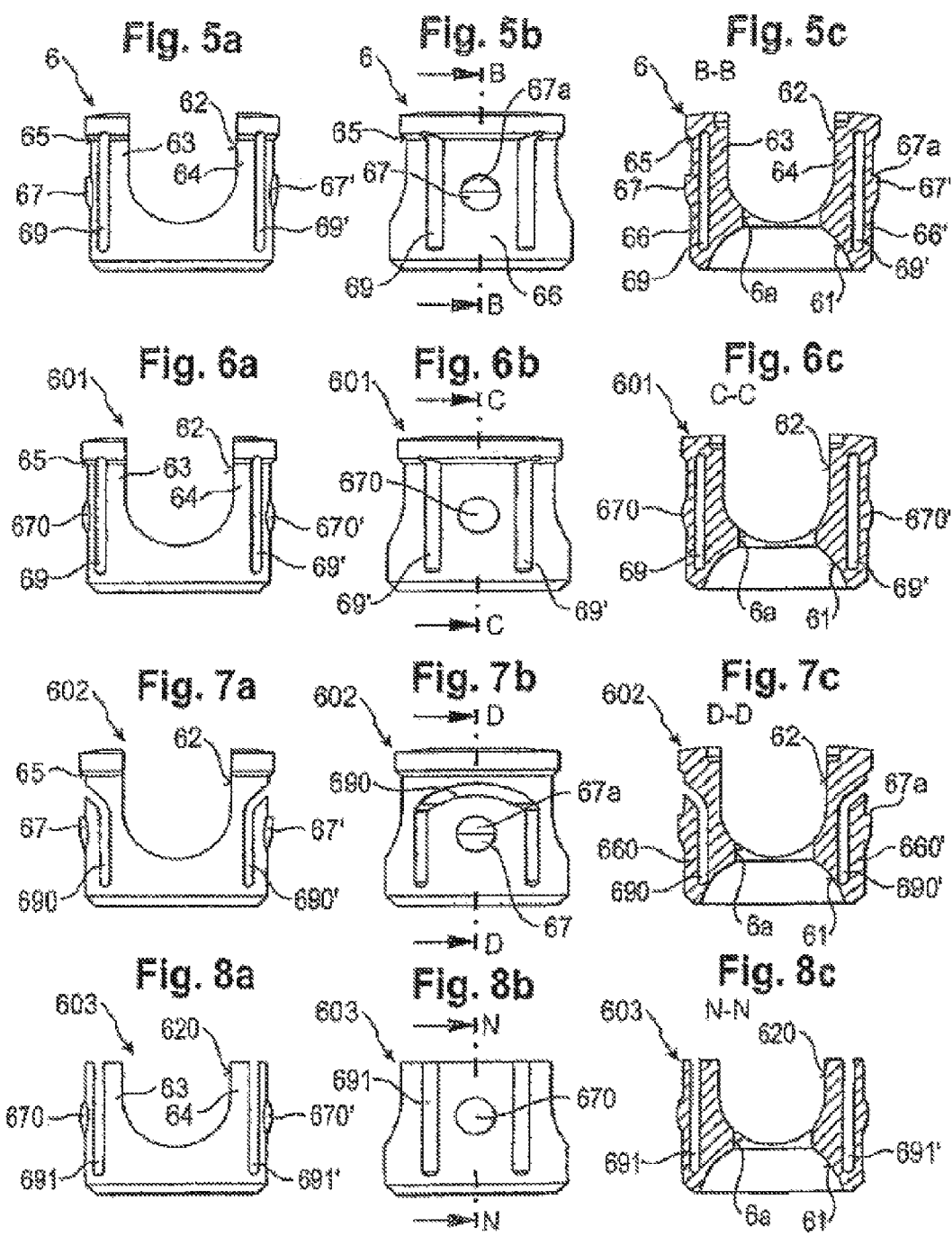

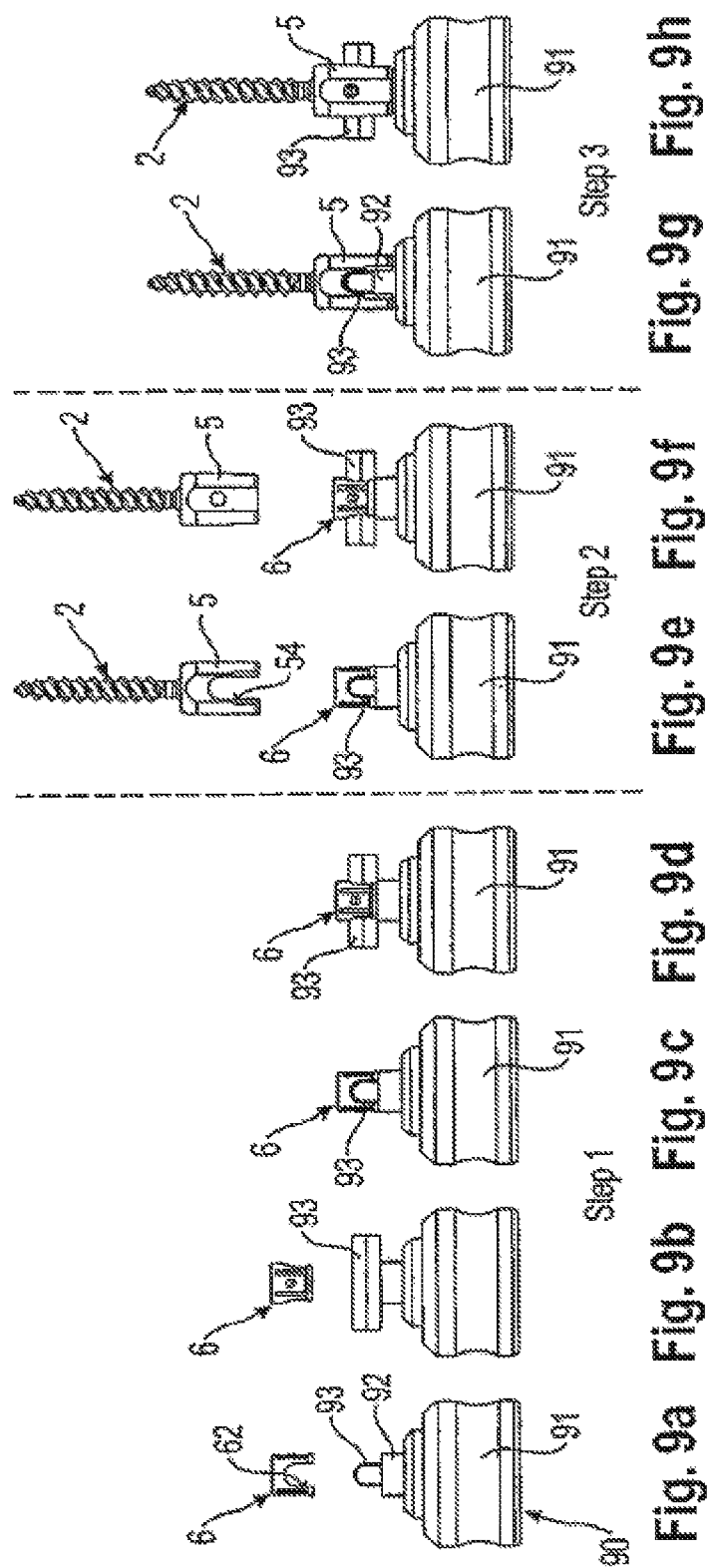

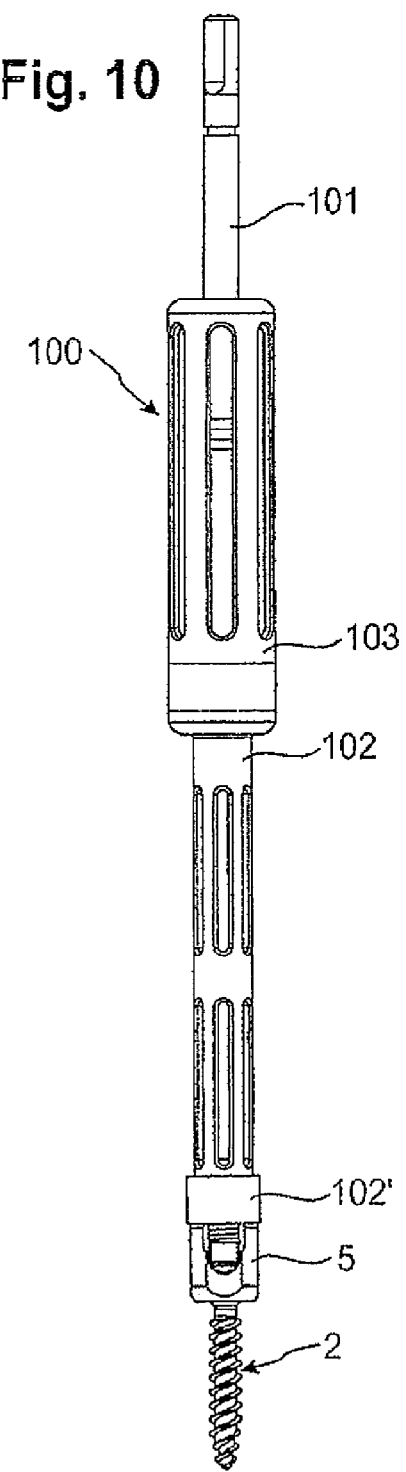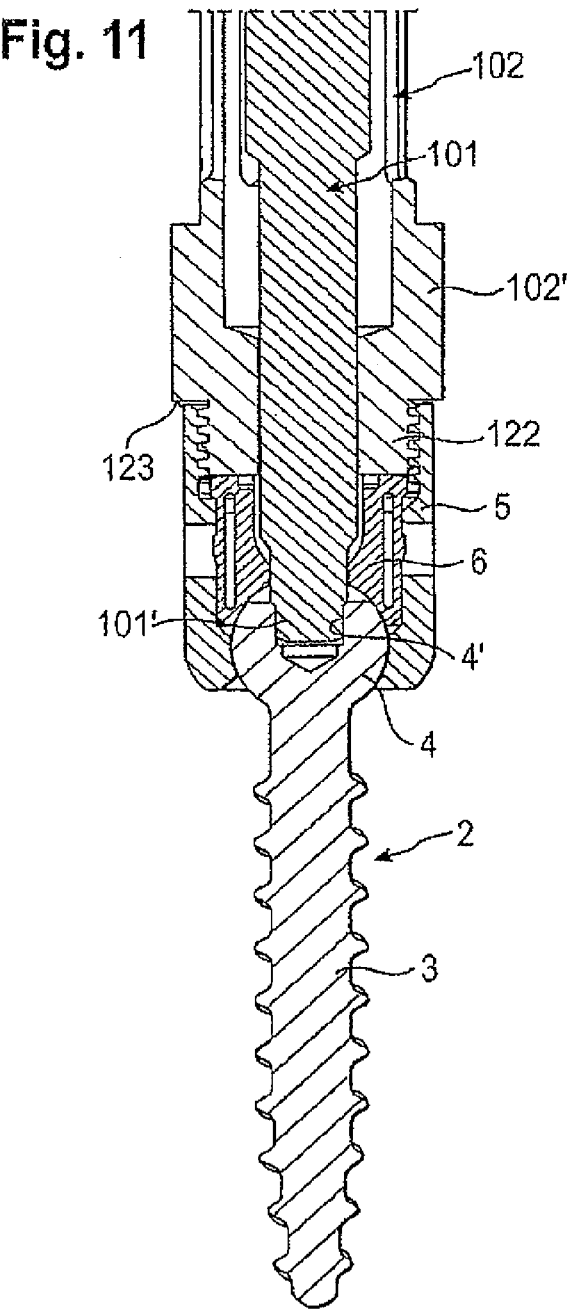

BONE ANCHORING DEVICE, TOOL AND METHOD FOR ASSEMBLING THE SAME AND TOOL FOR USE WITH THE SAME

CROSS-REFERENCE TO RELATED APPLICATION(S)

This application is a continuation of U.S. patent application Ser. No. 15/018,826, filed Feb. 8, 2016, which is a continuation of U.S. patent application Ser. No. 12/856,251, filed Aug. 13, 2010, now U.S. Pat. No. 9,254,150, which claims the benefit of U.S. Provisional Patent Application Ser. No. 61/235,493, filed Aug. 20, 2009, and claims priority from European Patent Application Number EP09168328.4, filed Aug. 20, 2009, the contents of which are incorporated herein by reference in their entirety.

BACKGROUND

The invention relates to a bone anchoring device for anchoring a stabilization rod in a bone or in a vertebra, an assembly tool and a method for assembling the bone anchoring device and an insertion tool for use with the bone anchoring device. The bone anchoring device includes an anchoring element, a receiving part for receiving a head of the bone anchoring element and for receiving a stabilization rod to be connected to the anchoring element. The anchoring element is pivotably connected to the receiving part and can be fixed at an angle by exerting pressure onto the head via a pressure element, which is arranged in the receiving part. The pressure element comprises a spring element that engages a portion of the receiving part so that it can be held in a position that allows pivoting of the anchoring element.

U.S. Pat. No. 5,716,356 describes a polyaxial bone screw including a screw element and a receiving part that is pivotably connected to the screw element and a pressure element to exert pressure onto the head of the screw element to fix the angle between the screw element and the receiving part. The receiving part has an U-shaped channel for receiving a stabilization rod. The pressure element comprises a cylindrical recess which is to be aligned with the U-shaped channel to receive the rod therein. In order to hold the pressure element in a position aligned with the U-shaped channel, the position of the pressure element is fixed by crimping through bores provided in the receiving part.

U.S. Pat. No. 5,672,176 describes another example of a polyaxial bone screw with a pressure element that is also held in place by crimp bores without impeding a sufficient movement of the pressure element to clamp the head.

US 2005/0080420 A1 describes a multiaxial bone screw that includes a screw element and a receiver member, a base member for retaining the screw element in the receiver member and a crown element exerting pressure onto the head of the screw element. The crown element comprises a snap-ring to assist in holding the crown element within the receiving part by interfering with a stop surface of the receiving part. The multiaxial bone screw is a so-called bottom loading type screw wherein the screw element is introduced from the bottom into receiving part.

WO 2006/116437 A2 describes a bone anchor for spinal fixation in the form of a polyaxial bone screw including a screw element, a housing, a sleeve and a collet arranged in the housing for exerting pressure onto the head of the screw element. The sleeve has retention tabs that snap into slots in opposite wall positions of the housing.

Usually, the polyaxial bone screws of the above-described type are delivered, for example by the manufacturer, in a pre-assembled condition. In this condition a specific screw element, e.g. a screw element having a specific length and shaft diameter or a specific thread form, is connected to a receiving part and the pressure element is arranged therein so that it cannot escape. For the surgery, the necessary number and types of such pre-assembled polyaxial bone screws are selected and provided in advance as a full set of implants.

SUMMARY

It is the object of the invention to provide a bone anchoring device, an assembly tool and a method of assembling the same and an insertion tool for use with the same which can be handled in a simple manner at the operation site or anywhere by the surgeon or other personnel.

The bone anchoring device has only a few parts. The parts are of a simple design. This provides for a lower cost of manufacturing and a convenient handling without sophisticated tools or machinery. It is possible to assemble the bone anchoring device by hand in any condition of the delivery after the parts have been manufactured and before the screw element is inserted into the bone. Therefore, the assembling of the polyaxial bone screw can be carried out by anybody, in particular by the surgeon or any personnel assisting him before or during surgery.

With the bone anchoring device, a modular system can be provided to allow the combination of various anchoring elements with any suitable receiver on demand, depending on the actual clinical requirements. This reduces the cost of polyaxial screws, reduces the inventory and gives the surgeon a substantial choice of implants. In addition, existing receiving parts may be upgraded with the pressure element to form the bone anchoring device according to the invention.

The assembly tool is simple and its function and handling is immediately apparent to the user. The correct mounting of the pressure element is easily recognizable. The insertion tool to be used for inserting the bone anchoring device permits a safe handling of the bone anchoring device during surgery.

Further features and advantages of the invention will become apparent from the description of embodiments by means of the accompanying drawings.

BRIEF DESCRIPTION OF THE DRAWINGS

FIG. 2 shows a side view of the bone anchoring device of FIG. 1 in an assembled state and rotated by 90°.

FIG. 3 shows a sectional view of the bone anchoring device according to FIG. 2 along line A-A.

FIG. 4 shows a sectional view of the receiving part of the bone anchoring device of FIG. 3.

FIGS. 5a) to c) show a side view, a side view rotated by 90° and a sectional view, respectively, of the pressure element of bone anchoring device according to the first embodiment.

FIGS. 6a) to c) show a side view, a side view rotated by 90° and sectional view, respectively, of a pressure element according to a second embodiment of the bone anchoring device.

FIGS. 7 a) to c) show a side view, a side view rotated by 90° and a sectional view, respectively, of a pressure element of a third embodiment of the bone anchoring device.

FIGS. 8 a) to c) show a side view, side view rotated by 90° and a sectional view, respectively, of the pressure element of a fourth embodiment of the bone anchoring device.

FIGS. 9 a) to h) show steps of assembling the bone anchoring device using the tool for assembling the bone anchoring device, each step in a side view and a side view rotated by 90°, respectively.

FIG. 10 shows a side view of the bone anchoring device together with a tool for inserting the bone anchoring device into the bone.

FIG. 11 shows an enlarged sectional view of a portion of the tool together with the bone anchoring device.

DETAILED DESCRIPTION

Figure 1:
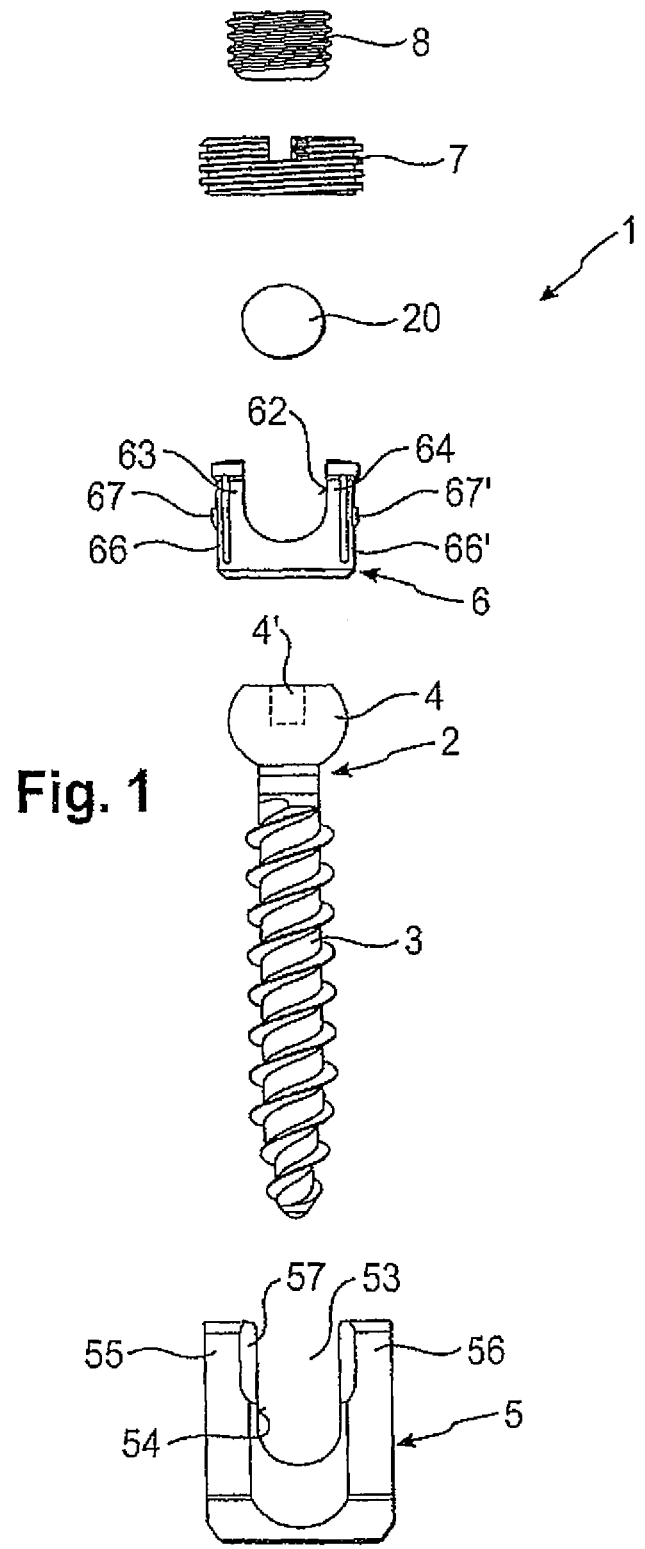
FIG. 1 shows an exploded side view of a first embodiment of the bone anchoring device.

The bone anchoring device 1 according to a first embodiment shown in FIGS. 1 to 5 includes a bone anchoring element, in this case a screw member 2 having a threaded shaft 3 and a head 4. The head 4 is, for example, shaped as a spherical segment. The head 4 has a recess 4' at its free end for engagement with a tool. The bone anchoring device further includes a receiving part 5 for connecting the screw member 2 to a rod 20. A pressure element 6 is arranged in the receiving part 5 on top of the head 4. For securing the rod 20 in the receiving part and for exerting pressure onto the pressure element 6, a two part locking device consisting of an outer screw 7 cooperating with the receiving part 5 and an inner screw 8 cooperating with the outer screw 7 is provided. It should be understood that the locking device shown is exemplary and can be realized in many other designs, in particular as a one part locking device and with different thread forms.

The receiving part 5 as shown in particular in FIGS. 1 to 4 is formed in one piece. In the example shown, it is substantially cylindrical and has a first bore 51 at one end thereof for passing the threaded shaft 3 therethrough. The bore 51 is followed by a seat portion 52 for accommodating the head 4 of the screw element. The seat portion 52 can be spherically-shaped or tapered or can have any other shape that allows accommodation of the head 4 so that the head 4 can pivot with respect to the receiving part 5. The seat portion 52 may have a threaded portion 52' to facilitate the insertion of larger diameter screw shafts. A second bore 53 opening towards the side opposite to the first bore 51 is provided for introducing the threaded shaft 3 together with the head 4. At the side of the second bore 53, the receiving part has a substantially U-shaped recess 54 by means of which two free legs 55, 56 are formed, which are the side walls of a channel for receiving the rod 20. An internal thread 57 is provided at the legs for cooperating with the outer screw 7 of the locking device. The second bore 53 can have a tapered section 57' at a transition between a larger diameter of the internal thread portion and a smaller diameter in a middle portion which provides a stop for the downward movement of the pressure element 6. Further, bores 58, 59 extending through the receiving part 5 are provided on opposite sides in the legs 55, 56. The diameter and cross-section of the bores 58, 59 are constructed so as to allow engagement with a portion of the pressure element 6 to be described below.

The pressure element 6 according to the first embodiment as particularly shown in FIGS. 1, 3 and 5a) to c) is formed in one piece. It is of substantially cylindrical construction and has an outer diameter that allows it to move in an axial direction within the second bore 53 of the receiving part 5. On its side facing the head 4 of the screw element 2, a spherical recess 61 is provided that is adapted to the size of the head 4. On its side opposite to the head 4, the pressure element has a cylindrical recess 62 adapted to receive the rod 20 therein. By means of the recess 62 two free legs 63, 64 are formed, which form the side walls of a channel for receiving the rod 20. In the embodiment shown, the depth of the recess 62 is larger than the diameter of the rod 20 so that the legs 63, 64 extend above the rod 20. At the end of the pressure element 6 opposite to the head 4, the pressure element may have a rim with an enlarged diameter, providing a shoulder 65 that abuts against tapered section 57' of the receiving part when the pressure element clamps the head 4.

The pressure element further comprises on the outer wall portion of each of the legs 63, 64 a spring element 66, 66' with a detent portion 67, 67' that cooperates with the receiving part 5, in particular with the bore 58, 59. The spring element 66, 66' is formed by means of a slot 69, 69' which is closed at the top and at the bottom and which extends completely through the legs 63, 64 in a direction parallel to the longitudinal axis of the channel, thereby leaving a portion of each leg 63, 64 spaced apart from the main body of the pressure element 6. At the outer wall of the spring element 66, 66', the detent portion 67, 67' is provided, which projects outward in such a way that the outer diameter of the pressure element 6 at the detent portion 67, 67' is larger than the inner diameter of the bore 53 of the receiving part 5. The overall size of the slot is larger than the cross-section of the bores 58, 59 in the receiving part. The depth and the overall size of the slot is such that the spring element 66, 66' can be moved resiliently into the space provided by the slot to such an extent, that the detent portion 67, 67' can be immersed therein. As can be seen in particular in FIGS. 5b) and c), the detent portion is asymmetric in a direction of the bore axis of the receiving part to allow insertion but prevent removal of the pressure element. The detent portion 67, 67' has a substantially circular base portion which goes over in a slanted manner into an upper portion which has an edge 67a, which abuts the upper wall of the bore 58, 59 such that the detent portion, once it is snapped into the bore 58, 59, as shown in FIG. 3, cannot be removed without using a specific tool.

Finally, the pressure element 6 has a coaxial bore 6a extending through it to allow access to the head 4 by a tool.

As shown in FIGS. 1 and 3, the outer screw 7 of the locking device can be screwed into the threaded legs of the receiving part 5 until it presses onto the upper rim of the pressure element 6, which moves the pressure element 6 downward until it presses onto the head 4 to lock the head 4 in the receiving part 5. The outer screw 7 has a threaded bore 71 into which the inner screw 8 can be screwed to clamp the rod 20.

The parts of the bone anchoring device are all made of a body compatible material such as titanium or stainless steel, a body compatible metal alloy, for example a Ti—Ni alloy, or a body compatible plastic material, such as PEEK. In particular, the pressure element 6 can be made of a body compatible plastic material which allows an easy manufacture and a safe function of the spring element.

A second embodiment of the bone anchoring device will be described with reference to FIGS. 1 to 4 and 6. The description of parts that are identical to the first embodiment will not be repeated. Like parts have the same reference numerals. The second embodiment differs from the first embodiment only by the design of the pressure element. As can be seen in FIGS. 6a) to 6c), the pressure element 601 differs from the pressure element 6 of the first embodiment only by the shape of the detent portion 670, 670'. The detent portion 670, 670' is symmetric in a direction of the bore axis of the receiving part 5 to allow insertion and removal of the pressure element 601. In the specific embodiment shown, the detent portion 670, 670' is shaped as a portion of a sphere. Since it is continuous in upward and downward direction, the detent portion 670, 670' can snap into the bore 58, 59 by a downward movement of the pressure element 601 and out of it by an upward movement. The recess 58, 59 at the receiving part 5 can be made smaller and adapted in shape to the shape of the detent portion so that the detent portion 670, 670' can snap into the recess 58, 59 and rest therein. The detent portion 670, 670' can have any other symmetric shape.

A third embodiment of the bone anchoring device will be described with reference to FIGS. 1 to 4 and 7. The description of parts that are identical to the first embodiment will not be repeated. Like parts have the same reference numerals. The third embodiment differs from the first embodiment only by the design of the pressure element. The pressure element 602 has slots 690, 690' that are open to the top so that the spring element 660, 660' is a lip being resiliently movable into the slot. With this construction, the flexibility of the spring element 660, 660' can be enhanced. As in the first embodiment, the detent portion 67 is asymmetric.

A fourth embodiment of the bone anchoring device will be described with reference to FIGS. 1 to 4 and 8. The description of parts that are identical to the first embodiment will not be repeated. Like parts have the same reference numerals. The fourth embodiment differs from the second embodiment only by the design of the pressure element. The pressure element 603 does not have the broadened rim with shoulder 65. Further, the slots 691, 691' at the legs 63, 64 are open to the top, thereby forming resilient lips as spring elements. The detent portion 670, 670' is symmetric as in the second embodiment. The recess 620 forming the channel for the rod has side walls that do not project above the rod. Hence, the pressure element can be used with a one-part locking device that simultaneously locks the rod and the head by acting onto the pressure element 603. The pressure element according to the fourth embodiment is easy to manufacture, has enhanced flexibility of the spring elements and is removable.

Features of the different pressure elements described in FIGS. 5 to 8 can be combined among each other to construct various other pressure elements.

Next, a tool for assembling the bone anchoring device and assembling steps are shown with reference to FIGS. 9a) to h). The first figure of each step shows a side view in direction of the rod axis and the subsequent second figure a side view perpendicular to the rod axis. The tool 90 includes a base portion 91, which is substantially cylindrical with a diameter that allows it to be placed onto a support, e.g. a table or the like (not shown). A cylindrical intermediate portion 92 extends coaxially from the base portion 91. The outer diameter of the intermediate portion 92 is such that the intermediate portion 92 can be introduced into the receiving part 5 as shown in FIG. 9g). At the end opposite to the base portion 91 a dummy rod portion 93 is provided at the intermediate portion 92. The dummy rod portion 93 has the diameter of the rod 20 so that the dummy rod portion 93 fits into the channel formed by the recess 62 in the pressure element 6. The rod axis of the dummy rod portion 93 extends perpendicular to the cylinder axis of the base portion 91.

In step 1, first, as shown in FIGS. 9a) and 9b), the tool is placed on a support such that the dummy rod portion 93 is on the top. Then, as shown in FIGS. 9c) and 9d), the pressure element is placed onto the dummy rod portion 93 with the U-shaped recess 62 facing downward. In step 2, the screw element 2 and the receiving part 5, which have been pre-assembled, are moved towards the tool with the U-shaped recess 54 of the receiving part facing downward and being aligned with the axis of the dummy rod portion 93. The pre-assembling of the screw element 2 and the receiving part 5 is carried out beforehand by introducing the screw element 2 from the top, i.e. from the second bore 53 into the receiving part 5 until the head 4 is seated in the seat portion 52. In step 3, the dummy rod portion 93 with pressure element 6 is introduced into the receiving part 5 by pressing the receiving part 5 down. The spring elements 66, 66' on the legs of the pressure element 6 as described above are pressed into the slots 69, 69' until the recesses 58, 59 in the receiving part are reached, which allows for the expansion of the spring elements 66, 66' and the catching of the detents 67, 67'. The catching of the detents 67, 67' is audible so that the user can be sure that the pressure element 6 is at the correct position. By means of the tool, the pressure element 6 can be easily inserted in the correct orientation so that its rod receiving recess 62 is aligned with the U-shaped recess 54 of the receiving part 5. Further, the pressure element 6 is held in the aligned position by the engagement of the spring elements 66, 66' in the recesses of the receiving part 5. In this position, the head 4 is still pivotable in the receiving part 5. The pressure element 6 is held so firmly that it cannot fall out of the receiving part 5 during handling but is still movable upon exertion of a force to clamp the head 4.

If a pressure element with a symmetric decent is used as described before, the pressure element can be removed from the pre-assembled position by pressing it out of the receiving part with the screw element.

Hence, the surgeon or any other person can easily preassemble a suitable combination of an anchoring element and a receiving part on demand and on-site.

Next, a tool for inserting the bone anchoring device into the bone and the use thereof is described with reference to FIGS. 10 and 11. The tool 100 includes a drive member 101 rotatably guided inside a tube-like counter-holding member 102, which is fixedly connected to a handle 103. The drive member 101 comprises a tip portion 101' that is engageable with the recess 4' of the head 4 of the screw element 2. The overall length of the drive member 101 is such that the drive member extends through the counter-holding member 102 and through the receiving part 5 and the pressure element 6 into the recess 4' of the head of the screw element 2. Therefore, a rigid connection between the bone anchoring device 1 and the drive member 101 is established. The counter-holding portion 102 has a tip portion 102' that is connectable to the receiving part 5. For this purpose, a threaded projection 122 is provided at the tip portion 102', which cooperates with the internal thread 57 on the legs of the receiving part 5. Between the threaded projection 122 and the tip portion 102', a shoulder 123 is formed, which acts as a stop when connecting the counter-holding member 102 to the receiving part 5. The threaded projection 122 has a length that is such that the threaded projection 122 touches the upper edge of the pressure element 6 when the counter holding member 102 is connected to the receiving part 5. This prevents the pressure element from being displaced upward by the counter force of the bone when the screw element 2 is inserted into the bone.

In use, after assembly of the bone anchoring device 1, the receiving part 5 is engaged with the counter-holding member 102 and the drive member 101 is connected to the recess 4' of the head 4. Then, the screw element 2 is inserted into the bone. Thereafter, the tool 100 is removed and the receiving part 5 is pivoted until it has the correct orientation to take up the rod 20. The rod 20, which connects several bone anchoring devices, is inserted and the outer screw 7 of the locking device is tightened on each bone anchoring device to move each pressure element 6 downward to clamp each head 4. The rod 20 is then fixed by the inner screw 8 of each locking device.

For the anchoring element all kinds of anchoring elements can be used and combined with a receiving part. These anchoring elements are e.g. screws of different length, with different diameters, cannulated screws, screws with different thread forms, nails, etc.

All kinds of receiving parts can be used in particular such with different locking devices, e.g. one part locking devices such as a single set screw that locks the rod and the head simultaneously, outer nuts, outer caps, bayonet locking devices or others. The engagement recesses for the spring elements of the pressure element need not to go through the wall completely but can be provided at the inner wall only. The shape of the receiving part is not limited to the embodiment shown. For example, the receiving part can have an asymmetric end portion for allowing a greater pivot angle of the screw member to one side.

The shape of the pressure element is also not limited to the embodiments shown. Only by way of example, the pressure element can be constructed so as to exert the pressure onto the head from the side of the head, e.g. via a conically tapering portion and/or can have a slotted portion clamping the head or other shapes.

Modifications of the tools described above are also conceivable. For example, the assembling tool can be constructed so as to clamp the pressure element.

What is claimed is:

1. A system comprising:
   a bone anchoring device comprising:
      an anchoring element having a shaft for anchoring in a bone and a head;
      a receiving part comprising a seat for receiving the head, a bore in communication with the seat, and an outer channel intersecting the bore for receiving a rod to be connected to the anchoring device; and
      a pressure element comprising an inner channel for receiving the rod, the pressure element being movable in the receiving part to exert pressure onto the head;
      wherein the anchoring element is pivotable with respect to the receiving part and can be fixed at an angle by exerting pressure via the pressure element onto the head; and
   a tool comprising:
      a dummy rod portion defining a first end of the tool, the dummy rod portion connectable to the pressure element and sized for engagement with the inner channel of the pressure element; and
      a second portion connected to the dummy rod portion, wherein the second portion is insertable into the bore of the receiving part and wider in at least one radial direction than a width of the inner channel of the pressure element, such that when the dummy rod portion engages the inner channel of the pressure element, the second portion is configured to abut against the pressure element.

2. The system of claim 1, wherein the tool further includes a base portion connected to the second portion on a side opposite the dummy rod portion.

3. The system of claim 2, wherein the base portion is wider in at least one radial direction than a maximum width of the second portion.

4. The system of claim 2, wherein the base portion and the second portion are coaxial, and wherein the dummy rod portion extends perpendicular to central axes of the base portion and the second portion.

5. The system of claim 1, wherein the receiving part comprises another bore on an opposite side of the seat for passing the shaft of the anchoring element therethrough.

6. The system of claim 1, wherein a locking device is provided that cooperates with the receiving part to lock the head and the rod separately.

7. The system of claim 1, wherein a locking device is provided that cooperates with the receiving part to lock the head and the rod simultaneously.

8. The system of claim 1, wherein the pressure element is insertable into the receiving part when the dummy rod portion of the tool engages the inner channel of the pressure element and the pressure element abuts against the second portion of the tool.

9. A method of assembling a bone anchoring device using a tool, the bone anchoring device comprising:
   an anchoring element having a shaft for anchoring in a bone and a head;
   a receiving part comprising a seat for receiving the head, a bore in communication with the seat, and an outer channel intersecting the bore for receiving a rod to be connected to the anchoring device; and
   a pressure element comprising an inner channel for receiving the rod, the pressure element being movable in the receiving part and configured to exert pressure onto the head;
   wherein the anchoring element is pivotable with respect to the receiving part and can be fixed at an angle by exerting pressure via the pressure element onto the head;
   the tool comprising a dummy rod portion defining a first end of the tool, the dummy rod portion connectable to the pressure element and sized for engagement with the inner channel of the pressure element, and a second portion connected to the dummy rod portion, wherein the second portion is insertable into the bore of the receiving part and wider in at least one radial direction than a width of the inner channel of the pressure element, such that when the dummy rod portion engages the inner channel of the pressure element, the second portion is configured to abut against the pressure element;
   the method comprising the steps:
      arranging the tool in a position in which the dummy rod portion is exposed;
      engaging the dummy rod portion with the inner channel of the pressure element with the pressure element abutting against the second portion of the tool;
      placing the receiving part onto the pressure element; and
      pressing the receiving part past the second portion of the tool until the pressure element is held in the receiving part.

* * * * *